(12) United States Patent
Waffenschmidt et al.

(10) Patent No.: US 8,423,129 B2
(45) Date of Patent: Apr. 16, 2013

(54) METHOD AND APPARATUS FOR INDUCTIVELY MEASURING THE BIO-IMPEDANCE OF A USER'S BODY

(75) Inventors: Eberhard Waffenschmidt, Aachen (DE); Andreas Brauers, Aachen (DE); Harald Reiter, Aachen (DE); Robert Pinter, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 478 days.

(21) Appl. No.: 11/915,750

(22) PCT Filed: May 16, 2006

(86) PCT No.: PCT/IB2006/051532
§ 371 (c)(1), (2), (4) Date: Nov. 28, 2007

(87) PCT Pub. No.: WO2006/129212
PCT Pub. Date: Dec. 7, 2006

(65) Prior Publication Data
US 2008/0221474 A1    Sep. 11, 2008

(30) Foreign Application Priority Data

May 31, 2005   (EP) .................................... 05104681

(51) Int. Cl.
*A61B 5/05*      (2006.01)
*A61B 5/00*      (2006.01)
*A61B 5/08*      (2006.01)
*A61B 5/103*     (2006.01)
*A61B 5/117*     (2006.01)

(52) U.S. Cl.
USPC .......... 600/547; 600/301; 600/533; 600/536; 600/587

(58) Field of Classification Search .................. 600/300, 600/301, 399, 409, 506, 533, 536, 546–548, 600/587, 595
See application file for complete search history.

(56) References Cited

U.S. PATENT DOCUMENTS 4,270,545 A   6/1981   Rodler
4,850,372 A   7/1989   Ko et al.
(Continued)

FOREIGN PATENT DOCUMENTS

| WO | 9612439 A1 | 5/1996 |
| WO | 0176475 A2 | 10/2001 |
| WO | 2004026136 A1 | 11/2007 |

OTHER PUBLICATIONS

"Eddy Current Based Flexible Sensor for Contactless Measurement of Breathing" by Richer et al, Instrumentation and Measurement Technology Conference, Ottawa, Canada, May 17-19, 2005.*

(Continued)

*Primary Examiner* — Sean P Dougherty
*Assistant Examiner* — Devin Henson (57) ABSTRACT

A method and apparatus for inductively measuring the bio-impedance of a user's body without complex circuitry. An apparatus is described for inductively measuring the bio-impedance of a user's body, wherein the apparatus includes a number of first inductors being adapted to induce an alternating magnetic field in the user's body and the apparatus further includes a number of second inductors being adapted to measure a secondary magnetic field in the user's body, wherein each of the number of first inductors overlaps at least one of the number of second inductors to form a number of measuring areas.

19 Claims, 6 Drawing Sheets

U.S. PATENT DOCUMENTS

| | | | |
|---|---|---|---|
| 5,010,772 A * | 4/1991 | Bourland et al. | 73/862.046 |
| 5,421,345 A | 6/1995 | Lekholm et al. | |
| 5,882,300 A * | 3/1999 | Malinouskas et al. | 600/300 |
| 6,480,111 B2 * | 11/2002 | Canady et al. | 340/573.1 |
| 6,564,079 B1 | 5/2003 | Cory et al. | |
| 2005/0054911 A1 * | 3/2005 | Nachman et al. | 600/411 |
| 2006/0125475 A1 * | 6/2006 | Sodickson et al. | 324/300 |

OTHER PUBLICATIONS

"Electrodeless Measurements of the Effective Resistivity of the Human Torso and Head by Magnetic Induction" by Tarjan et al, Oct. 1968, IEEE Transactions on Bio-medical Engineering, Voume BME-15 No. 4, 266-278.*

* cited by examiner

METHOD AND APPARATUS FOR INDUCTIVELY MEASURING THE BIO-IMPEDANCE OF A USER'S BODY

The present invention relates to a method and apparatus for inductively measuring the bio-impedance of a user's body. Furthermore, the invention relates to a bed comprising said apparatus.

The inductive measurement of bio-impedance is a known method to determine various vital parameters of a human body in a non-contact way. The operating principle is the following: Using an inductor loop, an alternating magnetic field is induced in a part of the human body. This alternating magnetic field causes eddy currents in the tissue of the body. Depending on the type and conductivity of tissue, the eddy currents are stronger or weaker. The eddy currents cause losses in the tissue, which can be measured as a decrease of the quality factor of the inductor loop. They also cause a secondary magnetic field, which can be measured as an inductivity change of the inductor loop or as an induced voltage in a second inductor loop.

The inductive measurement of the bio-impedance has been shown to allow the non-contact determination of several parameters, e.g. breathing action and depth, heart rate and change of the heart volume and blood glucose level, as well as fat or water content of the tissue.

Known devices can measure only small, well-defined parts of the human body. However, a spatially resolved measurement of the bio-impedance is desired, allowing a larger range of measurements. From the international patent application WO 2004/026136 A1 an apparatus is known, wherein the electromagnetic property of at least one region of a user's body is determined from the change in resonant property of at least one of a number of coils arranged in an array. A disadvantage of this and similar solutions is the very complex circuitry which is needed, if a spatially resolved measurement is to be carried out.

It is an object of the present invention to provide a method and apparatus for spatially resolved inductively measuring the bio-impedance of a user's body with a less complex circuitry.

This object is achieved according to the invention by an apparatus for inductively measuring the bio-impedance of a user's body, whereas the apparatus comprises a number of first inductors, said first inductors being adapted to induce an alternating magnetic field in the user's body, the apparatus further comprising a number of second inductors, said second inductors being adapted to measure a secondary magnetic field in the user's body, characterized in that each of the number of first inductors overlaps at least one of the number of second inductors to form a number of measuring areas.

This object is also achieved by a method of inductively measuring the bio-impedance of a user's body, the method comprising the steps of inducing an alternating magnetic field in the user's body by means of a number of first inductors, and measuring a secondary magnetic field in the user's body by means if a number of second inductors, whereas each of the number of first inductors overlaps at least one of the number of second inductors to form a number of measuring areas.

A basic idea of the present invention is to arrange two different sets of inductor loops in a way that the first set of inductors serve as field generating inductors (field inductors) and the second set of inductors serve as field sensing inductors (sensing inductors). Field inductors and sensing inductors cover each a certain area (total measuring area). Field inductors and sensing inductors are arranged in a manner such that during a measuring step only a small part of the total measuring area is scanned. In order to achieve this, field inductors and sensing inductors are arranged such that they overlap. At these spots small measuring areas are created. A number of these measuring areas are scanned during a number of (preferably time-sequentially) measuring steps to obtain a spatially resolved bio-impedance scan of the user's body. If the inductors show sufficient dimensions, spatially resolved measurements of bio-impedance are possible over a large area, e.g. covering a user's whole body. In other words, instead of using a large number of individual inductors, each being equipped with a number of cables, switches etc., a reduced number of inductors are used and an enhanced usability is reached by applying a new arrangement of said inductors and by applying a new cabling based on this arrangement. At the same time less electronics is needed, because of the new arrangement.

The object of the present invention is also achieved by a bed comprising said apparatus. A bed according to the present invention is then defined as a surface or any other device to rest on or to sit on etc., e.g. a conventional bed, a hospital bed, a couch, a conventional chair, a dentist's chair, a wheelchair, an (operating) table, etc. With this approach it is possible to carry out measurements when the user recovers in bed, e.g. at night. This gives reproducible results from one session to the other, because the measurement conditions are fairly well-defined. Thus, slow long-term changes can be monitored. As a further advantage the inventive solutions do not require the attachment of a device to the user's body. There is no risk of detaching such a device due to uncontrolled movements of the user during sleep. Additionally the user's comfort is improved.

These and other aspects of the invention will be further elaborated on the basis of the following embodiments, which are defined in the dependent claims.

According to a preferred embodiment of the invention, the number of first inductors and the number of second inductors are arranged in a way that they form a matrix of measuring areas. In other words, a kind of grid is formed, said grid comprising all measuring areas, thus covering the total measuring area of the apparatus. Such a matrix solution needs significantly less electronics, e.g. fewer switches etc. Preferably, the grid is of a regular shape, e.g. substantially rectangular, for covering a bed or the like. Thus, according to another embodiment of the invention, the number of first inductors are preferably arranged substantially in a first direction and the number of second inductors are arranged substantially in a second direction, whereas the second direction is substantially orthogonal to the first direction.

According to another preferred embodiment of the invention, a number of switches are assigned to the number of first and/or second inductors in a way that each of the number of first and/or second inductors can be controlled separately. In this way, the information from the inductors, i.e. from each measuring area, can be obtained time-sequentially.

According to another preferred embodiment of the invention, the number of first and/or second inductors are arranged in a way that at least one of the resulting measuring areas shows a substantially regular shape. The shape may be e.g. quadrangular, in particular rectangular, quadratic or trapezoid in order to provide a measuring arrangement which shows the shape of a regular grid.

According to another preferred embodiment of the invention, the number of first and/or second inductors are arranged in a way that at least one of the resulting measuring areas shows an irregular shape. The shape may be defined e.g. by curves and straight lines in order to provide a measuring arrangement which shows the shape of a distorted grid. Especially if certain regions are of greater interest than others, this embodiment shows a large number of advantages. In this case the density of the intersection points between the number of first and second inductors in a first measuring region of the apparatus is different from the density of those intersection points in a second measuring region of the apparatus. In other words the surface area of the number of measuring areas is not constant throughout the measuring arrangement. This means that the shape of each inductor and thus the shape of each measuring area may vary for different positions in the total measuring area. A high density of intersection points means that a large scanning resolution can be achieved. At the same time the surface area of corresponding measuring areas is small, leading to a loss of depth information. The density of intersection points and the form of the measuring areas is preferably selected depending on the standard position of the user, e.g. during sleep and/or depending on the kind of measurements to be carried out.

According to another preferred embodiment of the invention, the apparatus comprises a number of first conductor elements, said first conductor elements being freely connectable to each other to form a first inductor and/or a number of second conductor elements, said second conductor elements being freely connectable to each other to form a second inductor. In other words, conductor elements (e.g. wires) are arranged in a way that they are freely connectable to each other in order to form field inductors and/or sensing inductors of different shape and thus in order to form measurement areas of different shape. This means that the overall number of conductors and electronics can be further reduced, leading to a very simple and cheap measuring arrangement.

The apparatus according to the present invention is preferably used with a bed. In this case a first and/or second inductor preferably comprises a structured conductor element on a flexible substrate, said structured conductor element being preferably made of copper, and said flexible substrate is preferably attached to a bed sheet. By using a single flexible substrate, the handling of said substrate and the attaching of the substrate to the bed sheet is very easy. Alternatively, each inductor loop can be manufactured on its own substrate. These smaller substrates can e.g. be woven crosswise into the fabric of a bed sheet.

In another embodiment a first and/or second inductor comprises a flexible conductor element, preferably in the form of a wire, said flexible conductor element being preferably integrated into a bed sheet, e.g. by means of stitching or weaving. This solution is the most flexible and the most comfortable solution for the user.

These and other aspects of the invention will be described in detail hereinafter, by way of example, with reference to the following embodiments and the accompanying drawings in which.

Figure 1:
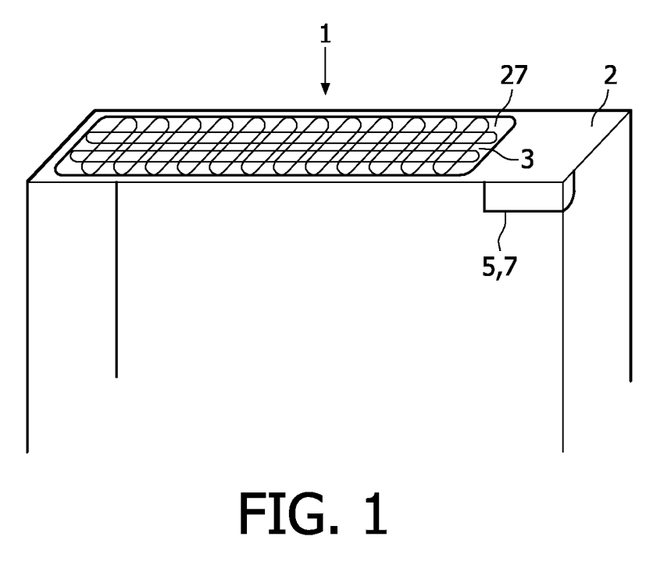
FIG. 1 is a schematic view of a bed comprising an apparatus according to the invention.

FIG. 1 illustrates a contactless medical diagnostic apparatus 1 according to the invention. The apparatus 1 is integrated with a bed 2. The apparatus 1 comprises an array of coils 3 distributed over the area of the bed 2. The array of coils 3 is intended to measure spatially resolved the bio-impedance of the human body (not shown) on the bed 2. The apparatus 1 allows an easy and comfortable diagnosis of vital parameters like the heart rate, tissue water content or blood glucose level to supervise a user during recovery in the bed 2 without the need of applying any kind of devices to a user's body.

Figure 2:
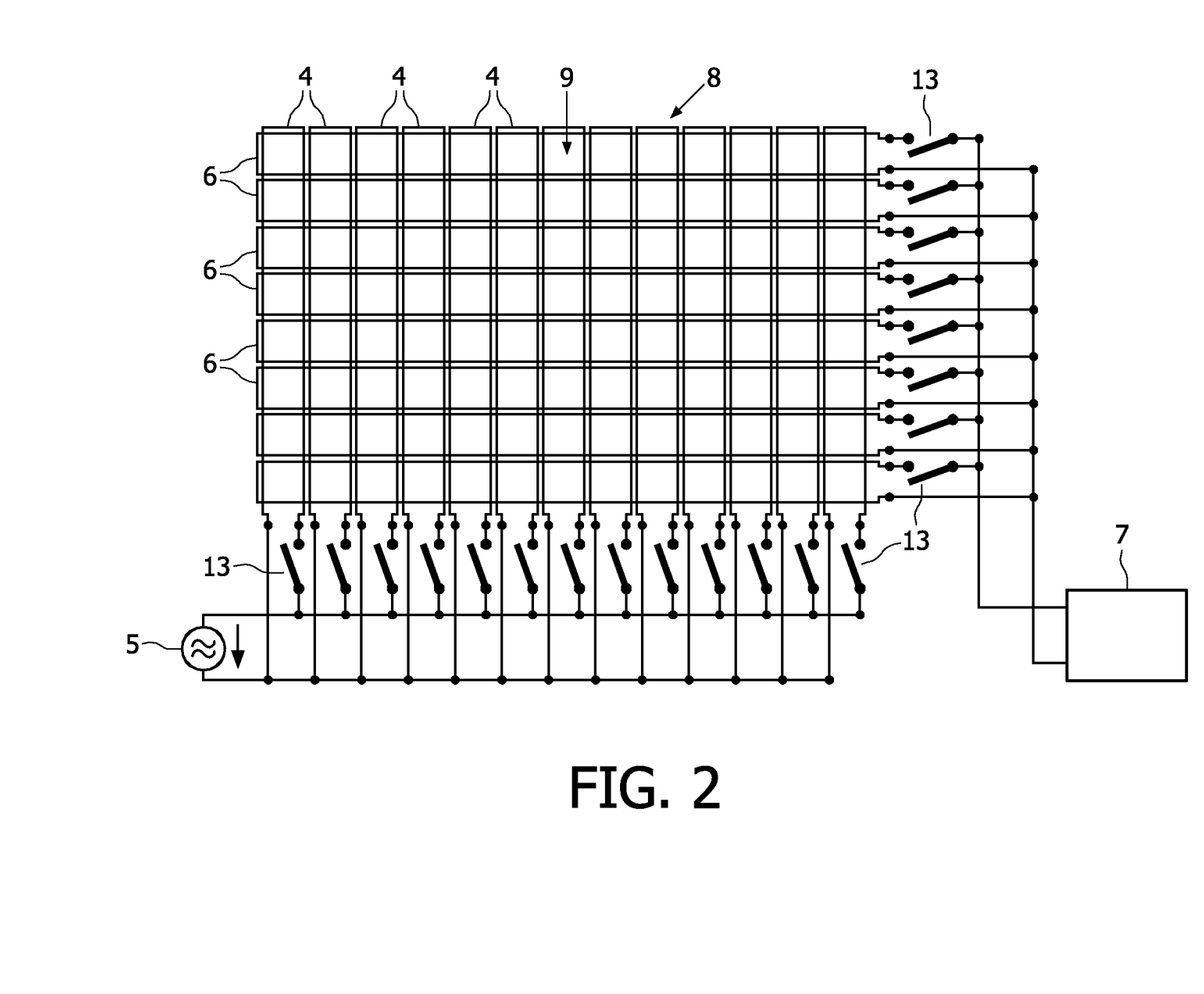
FIG. 2 is a schematic view of an apparatus according to a first embodiment.

As illustrated in FIG. 2 the apparatus 1 comprises a number of first coils, said first coils being adapted to induce an alternating magnetic field in the user's body. In other words, the first coils serve as field generating coils (field coils) 4. For this purpose the field coils 4 are connectable to a power source 5.

The apparatus 1 further comprises a number of second coils, said second coils being adapted to measure a secondary magnetic field in the user's body, said secondary magnetic field being caused by eddy currents in the tissue of the body. In other words the second coils serve as field sensing coils (sensor coils) 6. For this purpose the sensor coils 6 are connectable to a detector unit 7. The detector unit 7 is adapted to receive and store the measured signals. The detector unit 7 preferably comprises a computer adapted to process measured signals and to compute measuring results. Such measuring results are stored in a data storage and/or are transferred to a display (not shown) or to a communication interface (not shown) in order to be transferred to an operator or physician.

Field coils 4 and sensor coils 6 are arranged such that they form a stripe matrix 8. Field coils 4 as well as sensor coils 6 are illustrated in a simplified way, in a sense that each coil is shown to comprise two wires (an upward-running wire and a downward-running wire). In reality each wire comprises a number of turns.

As shown in FIG. 2 the arrangement of coils 4, 6 have the form of a grid. The matrix 8 comprises a first array of field coils 4 and a second array of sensor coils 6. The apparatus 1 is characterized in that each of the number of field coils 4 overlaps at least one of the numbers of sensor coils 6 to form a number of measuring areas 9.

Figure 3:
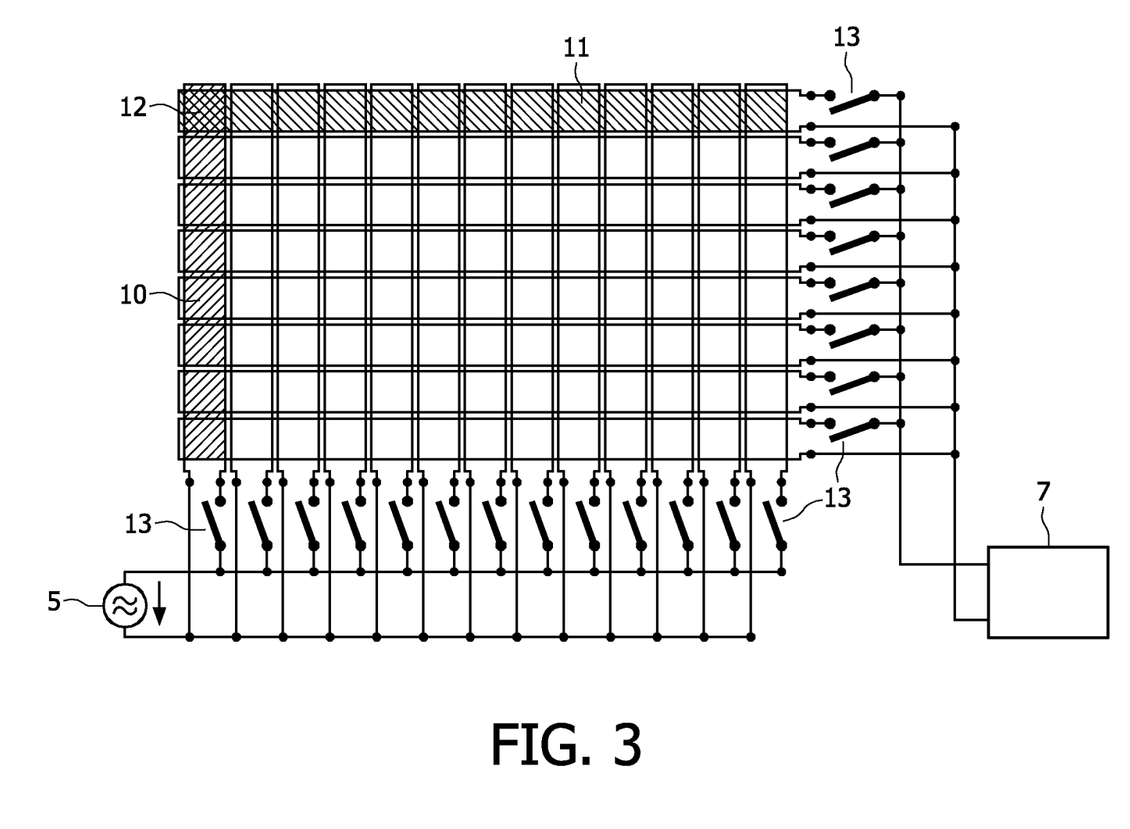
FIG. 3 is a schematic view of an apparatus according to a first embodiment illustrating the operation of the apparatus.

As illustrated in FIG. 3, in a first step a magnetic flux is induced in only a single long stripe 10 of an inductor loop of the first array, i.e. the array of field coils 4. In FIG. 3 this stripe 10 is running vertically and is hatched for better understanding. Subsequently a single long stripe 11 of an inductor loop of the second array, i.e. the array of sensor coils 6, is selected to measure the magnetic flux induced in this stripe 10. In FIG. 3 this stripe 11 is running horizontally and is hatched for better understanding.

Only the area 12, where the two stripes 10, 11 overlap contributes to the measurement. In this way, the measurement allows the detection of the bio-impedance only in the small measuring area 12. The dimensions of field coils 4 and sensor coils 6 define the total measuring area of the apparatus 1, preferably covering a complete bed sheet. Preferably all measuring areas 12 are scanned during a number of time-sequentially measuring steps to obtain a spatially resolved bio-impedance scan of the user's body.

A number of switches 13 are connected to the field coils 4 and sensor coils 6 respectively in a way that each of these coils 4, 6 can be addressed separately. In other words each coil can be operated independently of another coil.

In the present example thirteen field coils 4 and eight sensor coils 6 are used. This results in a total number of 104 measuring areas 12. If for example each field coil 4 is switched on for a time period of one second, each of the sensor coils 6 may sense for 125 milliseconds information from the respective measuring area 12, which it forms together with the field coil 4. Subsequently the next field coil 4 is switched on etc. As a result, after operating all thirteen field coils 4, i.e. after an operating time of thirteen seconds, a complete bio-impedance scan has been performed covering the whole bed sheet area. In other words, at least one and preferably all field coils 4 are switched on (and off) in a time-sequential manner and for each operating field coil 4 at least one and preferably all sensor coils 6 are switched on (and off) in a time-sequential manner. The results of such a bio-impedance scan allow a spatially resolved analysis of the measuring values.

Figure 4:
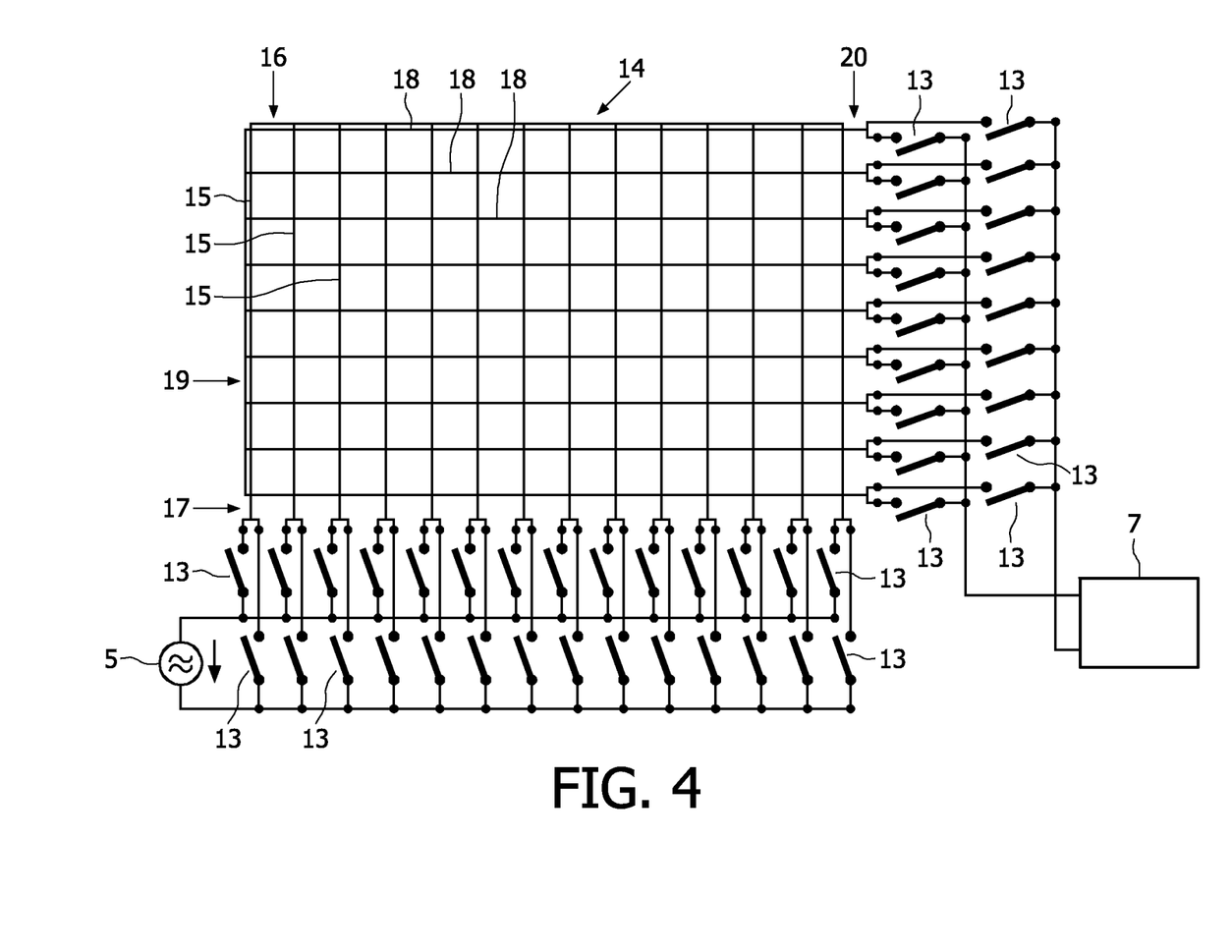
FIG. 4 is a schematic view of an apparatus according to a second embodiment.

In another embodiment of the invention a comb-like matrix 14 is used, see FIG. 4. A number of first tracks 15 are provided then. In FIG. 4 the tracks 15 are running vertical in a comb-like structure, i.e. they are connected to each other at one end 16 and freely connectable to each other at the other end 17 by means of switches 13 to form a field coil 4. Additionally, a number of second tracks 18 are provided. The tracks 18 are running horizontally in FIG. 4 in a comb-like structure, i.e. they are connected to each other at one end 19 and freely connectable to each other at the other end 20 by means of switches 14 to form a sensor coil 6. In this way, field coils 4 and/or sensor coils 6 of different shape can be formed. In other words, fewer tracks are needed to form the coils, making their manufacturing easier. Again switches 13 are connected to the tracks 15, 18 in a way that each coil 4, 6 to be formed by the tracks 15, 18 can be addressed separately.

Figure 5:
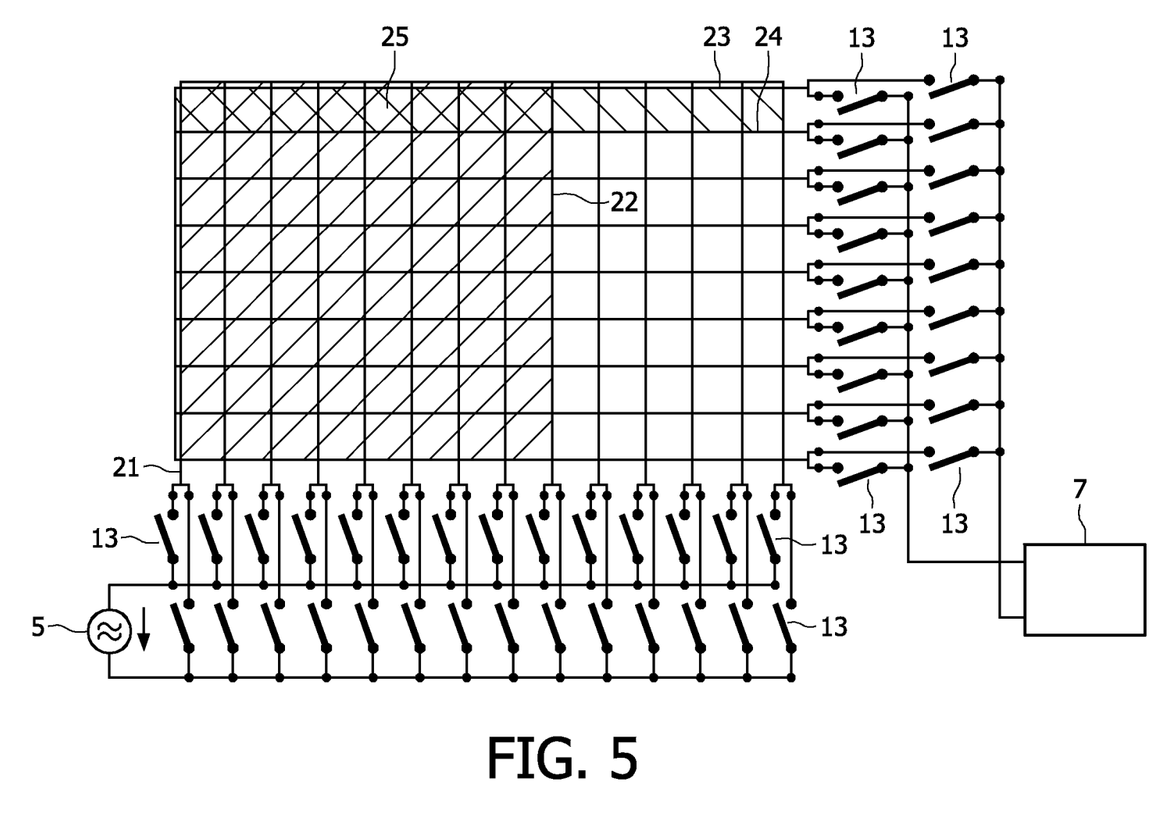
FIG. 5 is a schematic view of an apparatus according to a second embodiment illustrating the operation of the apparatus.

For example the very first (upward-running) track 21 is connected to a (downward-running) track 22 in the middle of the arrangement to form a field coil 4, see FIG. 5. Thus the resulting field coil 4 covers 64 of the original (quadratic) measuring areas. For the purpose of illustration the surface area of the resulting field coil 4 is hatched.

At the same time the size of the sensor coil 6 can be chosen. If, for example, the sensor coil 6 is formed by two adjacent tracks 23, 24, the resulting measuring area 25, which is formed by the overlap between the field coil 4 and the sensor coil 6 covers eight of the original (quadratic) measuring areas. For the purpose of illustration the surface area of the resulting field coil 6 is hatched.

Using such an arrangement, any coil size can be provided, depending on the kind of measurement and the desired resolution. If small measuring areas are created, the scanning resolution is high. At the same time only a small amount on depth information can be detected. On the other hand, if large measuring areas are used, the scanning resolution is low coupled with a high depth of field.

The use of electrical connections, e.g. switches 13 etc., and the circuit design may vary from the embodiment illustrated.

As shown in FIGS. 2, 3, 4 and 5 field coils 4 and sensor coils 6 are preferably arranged such, that they are substantially orthogonal to each other. This results in a regularly shaped matrix 8, 14 with rectangular measuring areas 12, 25. The resolution of the bio-impedance measurement is constant over the whole arrangement.

Figure 6:
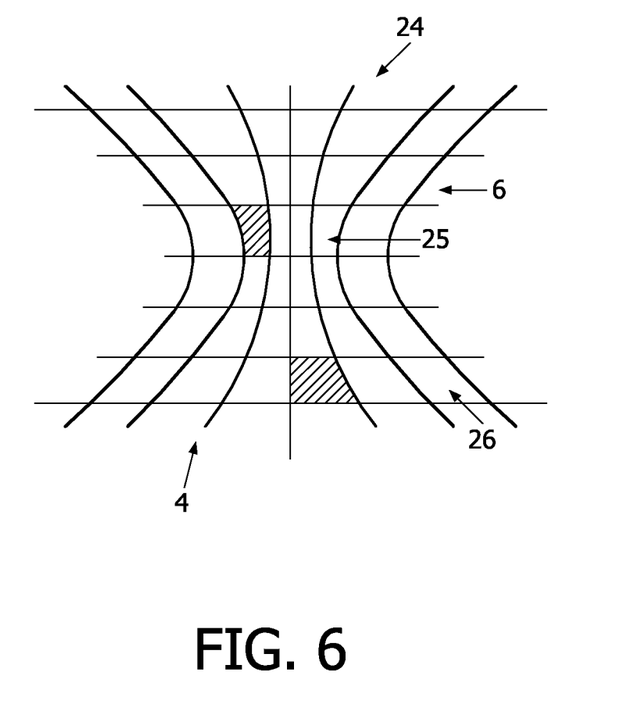
FIG. 6 is a schematic view of an irregularly shaped measuring grid.

In another embodiment of the invention, as illustrated in FIG. 6, the coils are arranged in a way that a distorted grid 24 of measuring areas is created. For reasons of clarity no switches or the like are shown. Only the arrangement of coil tracks is shown.

The density of the intersection points between the vertically running field coils 4 and horizontally running sensor coils 6 in a first measuring region 25, e.g. in the middle of the bed, is larger than the density of those intersection points in a second measuring region 26, e.g. near the edge of the bed. As illustrated by means of hatched example areas, the measuring areas have different surface areas depending on their location, i.e. the resolution of the bio-impedance measurements is different. In the illustrated embodiment a large scanning resolution is achieved in the first measuring region 25, whereas a good depth field is achieved in the second measuring region 26.

The field and sensor coils 4, 6 are preferably made of structured copper on a large flexible substrate 27 like polyamide (flexfoil), which is attached to the bed sheet, see FIG. 1. Alternatively, the inductor loops can be woven or stitched with thin wire into the bed sheet. In this case the thin wire has a thin electrical insulation layer to avoid short circuits on points where two wires cross each other. All solutions can be made waterproof, so that the bed sheet is washable. The source and detector electronics 5, 7 is preferably integrated into the bed sheet as well. In this case it must be sealed watertight. In another version the electronics can be detached from the bed sheet prior to washing. Then the contacts must be waterproof. Alternatively, source 5 and detector 7 are attached to the bed in a separate box or the like, as illustrated in FIG. 1.

The apparatus 1 as described above is preferably used to detect the heart rate. In addition, the array of sensor coils 6 can be used to automatically select and track the position of the measuring area 12, 25 with the best signal quality. By measuring the time delay of the heart rate signal between two measuring areas (e.g. a first measuring area near the lower end of the user's arm and a second measuring area near the upper end of that arm), it is possible to gain information on the blood pressure of the user's body. The breathing action of the user can be monitored as well. This is helpful for the monitoring of small children, but it could also give an indication of the sleep quality. Additionally the movement of the body can be monitored. The activity of the person also gives an indication of the sleep quality. Furthermore, to get a better data correlation it can be detected whether the person sleeps or is awake. Bio-impedance measurements with the present apparatus 1 can also be used to monitor the glucose content of the blood. The apparatus 1 can be coupled to an alarm system (not shown) that wakes up the person in case of a hypoglycaemic situation. Bio-impedance measurements can also be used to detect the water or fat content of tissue. The measurement situation in a bed 2 is well reproducible between different sessions. Therefore, it allows a good comparison over a longer time period. The success of a diet by measuring the body fat content or the long-term increase of the water content in the tissue due to a possible insufficient heart operation can thus be monitored very well.

For all applications of the apparatus according to the present invention, as described above, the detector 7 can be used. Preferably the detector 7 comprises a computer (not shown), which is adapted to execute a computer program comprising computer instructions to derive data according to the desired application from the measuring signals, when the computer program is executed in said computer. The technical effects necessary according to the invention can thus be realized on the basis of the instructions of the computer program in accordance with the invention. Preferably the computer program comprises computer instructions to separately control each of the number of field 4 and/or sensor coils 6. In particular the computer program comprises computer instructions to operate at least one and preferably all field coils 4 in a time-sequential manner and to operate for each operating field coil 4 at least one and preferably all sensor coils 6 in a time-sequential manner, so that a spatially resolved measurement of bio-impedance can be achieved.

Such a computer program can be stored on a carrier such as a CD-ROM or it can be available over the internet or another computer network. Prior to execution, the computer program is loaded into the computer by reading the computer program from the carrier, for example by means of a CD-ROM player, or from the internet, and storing it in the memory of the computer. The computer includes inter alia a central processor unit (CPU), a bus system, memory means, e.g. RAM or ROM, storage means, e.g. floppy disk or hard disk units and input/output units.

It will be evident to those skilled in the art that the invention is not limited to the details of the above illustrative embodiments, and that the present invention may be embodied in other specific forms without departing from the spirit or essential attributes thereof. The present embodiments are therefore to be considered in all respects to be illustrative and not restrictive, the scope of the invention being indicated by the appended claims rather than by the above description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit may fulfil the functions of several means recited in the claims. Any reference signs in the claims shall not be construed as limiting the claim concerned.

REFERENCE NUMBER LIST 1 apparatus
2 bed
3 array of coils
4 field coil
5 power source
6 sensor coil
7 detector unit
8 stripe matrix
9 measuring area
10 stripe
11 stripe
12 measuring area
13 switch
14 comb matrix
15 first track
16 track end
17 track end
18 second track
19 track end
20 track end
21 upward-running track
22 downward-running track
23 measuring area
24 distorted grid
25 first measuring region
26 second measuring region
27 substrate

The invention claimed is:

1. An apparatus for inductively measuring the bio-impedance of a user's body, the apparatus comprising:
a number of first inductors, the first inductors being adapted to induce an alternating magnetic field in the user's body, and
a number of second inductors, the second inductors being adapted to measure a secondary magnetic field in the user's body,
wherein each of the number of first inductors overlaps at least one of the number of second inductors at intersection points to form a number of measuring areas,
wherein the number of first inductors are arranged in a first direction on a predetermined plane of a substrate and the number of second inductors are arranged in a second direction on the predetermined plane of the substrate, and
wherein the density of the intersection points between the number of first and second inductors in a first measuring area is different from the density of the intersection points in a second measuring area.

2. The apparatus as claimed in claim 1, wherein the number of first inductors and the number of second inductors are arranged in a way that they form a matrix of measuring areas.

3. The apparatus as claimed in claim 1, wherein the second direction is substantially orthogonal to the first direction.

4. The apparatus as claimed in claim 1, wherein a number of switches are assigned to the number of one of first and second inductors in a way that each of the number of one of first and second inductors can be controlled separately.

5. The apparatus as claimed in claim 1, the number of one of first and second inductors are arranged in a way that at least one of the resulting measuring areas shows a substantially regular shape.

6. The apparatus as claimed in claim 1, wherein the number of one of first and second inductors are arranged in a way that at least one of the resulting measuring areas shows an irregular shape.

7. The apparatus as claimed in claim 1, wherein the apparatus comprises one of a number of first conductor elements, the first conductor elements being freely connectable to each other to form a first inductor and a number of second conductor elements, the second conductor elements being freely connectable to each other to form a second inductor.

8. The apparatus as claimed in claim 1, wherein the apparatus is included in a bed, and wherein one of a first and second inductor comprises a structured conductor element on a flexible substrate, the structured conductor element being made of copper, and the flexible substrate being attached to a bed sheet.

9. The apparatus as claimed in claim 1, wherein the apparatus is included in a bed, and wherein one of a first and second inductor comprises a flexible conductor element, the flexible conductor element being integrated into a bed sheet.

10. The apparatus of claim 1, wherein each of the number of first and second inductors are selectively controllable so that only one of the first inductors and one of the second inductors are activated, wherein the measuring area is a location where the one of the first inductors and the one of the second conductors overlap.

11. A method of inductively measuring the bio-impedance of a user's body, the method comprising the steps of:
inducing an alternating magnetic field in the user's body by means of a number of first inductors, and
measuring a secondary magnetic field in the user's body by means of a number of second inductors,
wherein each of the number of first inductors overlaps at least one of the number of second inductors at intersection points to form a number of measuring areas,
wherein the number of first inductors are arranged in a first direction on a predetermined plane of a substrate and the number of second inductors are arranged in a second direction on the predetermined plane of the substrate, and
wherein the density of the intersection points between the number of first and second inductors in a first measuring area is different from the density of the intersection points in a second measuring area.

12. The method as claimed in claim 11, wherein each of the number of one of first and second inductors is controlled separately.

13. The method as claimed in claim 11, comprising:
operating at least one of the first inductors in a time-sequential manner, and
during operation of each first inductor, operating at least one of the second inductors in a time-sequential manner.

14. The method of claim 11, wherein in the inducing step only one of the first inductors is activated to induce the magnetic filed and in the measuring step only one of the second inductors is activated to measure the secondary magnetic field, wherein the measuring area is a location where the one of the first inductors and the one of the second conductors overlap.

15. An apparatus for inductively measuring the bio-impedance of a user's body, the apparatus comprising:
a plurality of first inductors that induce an alternating magnetic field in a user's body;
a plurality of second inductors that measure a secondary magnetic field in a user's body; and
one or more measurement areas formed by overlap of at least one of the first inductors and at least one of the second inductors at intersection points;
wherein the one or more measurement areas can be modified in shape or size depending on a desired application of the apparatus,
wherein the number of first inductors are arranged in a first direction on a predetermined plane of a substrate and the number of second inductors are arranged in a second direction on the predetermined plane of the substrate, and
wherein the density of the intersection points between the number of first and second inductors in a first measuring area is different from the density of the intersection points in a second measuring area.

16. The apparatus of claim 15, wherein the apparatus is formed as part of a bed.

17. The apparatus of claim 15, wherein the plurality of first inductors and the plurality of second inductors are arranged to form a matrix of measurement areas.

18. The apparatus of claim 15, further comprising means for sequentially measuring different measurement areas.

19. The apparatus of claim 15, wherein each of the number of first and second inductors are selectively controllable so that only one of the first inductors and one of the second inductors are activated, wherein the measuring area is a location where the one of the first inductors and the one of the second conductors overlap.

\* \* \* \* \*